United States Patent [19]

Green et al.

[11] Patent Number: 5,438,709
[45] Date of Patent: Aug. 8, 1995

[54] LUBRICOUS GLOVES AND METHOD FOR MAKING LUBRICOUS GLOVES

[75] Inventors: Richard Green, Livingston, N.J.; Glenn F. Stockum; Mao-Ching Chen, both of Arlington, Tex.

[73] Assignee: Johnson & Johnson Orthopaedics, Inc., Raynham, Mass.

[21] Appl. No.: 854,146

[22] Filed: Mar. 20, 1992

[51] Int. Cl.⁶ ............................................. A41D 19/00
[52] U.S. Cl. .......................................... 2/167; 2/168; 524/55; 524/503
[58] Field of Search ...................... 2/161.7, 161.8, 168, 2/161.6, 167, 159, 163; 524/908, 55, 503, 354, 492; 525/57; 428/497, 500, 522, 446; 106/14.41, 14.44; 602/1, 3, 32, 901

[56] References Cited

U.S. PATENT DOCUMENTS

| | | | |
|---|---|---|---|
| 4,197,371 | 4/1980 | Holst et al. | 521/84.1 |
| 4,548,844 | 10/1985 | Podell et al. | 2/168 |
| 4,851,282 | 7/1989 | Shimizu et al. | 428/913 |
| 4,853,978 | 8/1989 | Stockum | 2/167 |
| 5,024,852 | 6/1991 | Busnel et al. | 2/168 |
| 5,079,348 | 1/1992 | Clare et al. | 536/3 |

FOREIGN PATENT DOCUMENTS

| | | |
|---|---|---|
| 399775 | 11/1990 | European Pat. Off. |
| 2315382 | 1/1977 | France . |
| 2840197 | 3/1980 | Germany . |

*Primary Examiner*—Clifford D. Crowder
*Assistant Examiner*—Amy Brooke Vanatta
*Attorney, Agent, or Firm*—Joseph F. Shirtz

[57] ABSTRACT

A modified elastomeric glove is disclosed having a lubricous coating made up of polyvinyl alcohol and a thickening agent. The thickening agent is initially added in order to increase the processability of the polyvinyl alcohol coating in order to prevent runbacks and drips during the manufacturing process. A hydroscopic thickener may be used. The polyvinyl alcohol coating becomes lubricous when wetted in a water bath and therefore becomes particularly useful in applying a water-activated resin casting material for forming orthopaedic casting bandages.

3 Claims, 2 Drawing Sheets

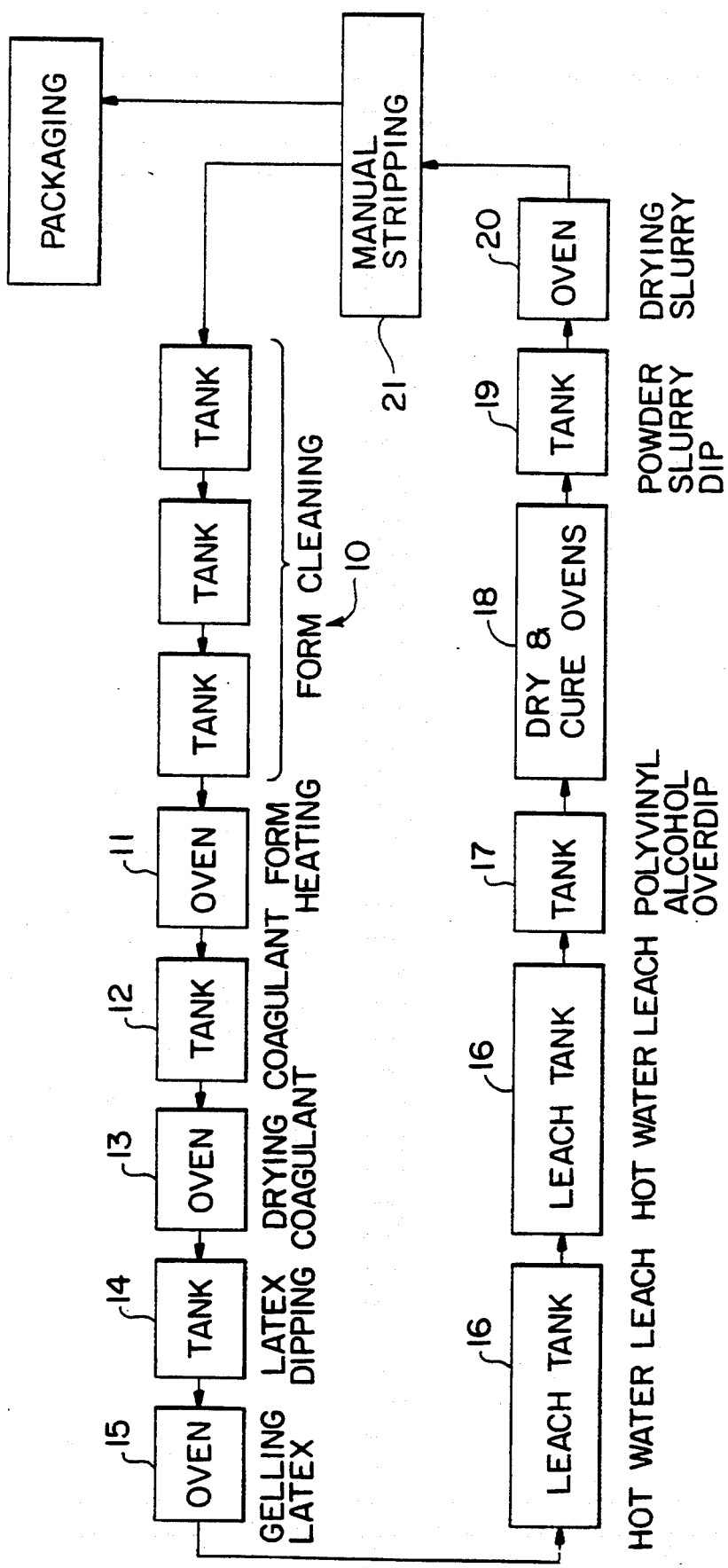

LUBRICOUS GLOVES AND METHOD FOR MAKING LUBRICOUS GLOVES

FIELD OF THE INVENTION

The present invention relates to an improved method for making lubricous gloves for applying orthopaedic casting bandages of the type used to form orthopaedic casts and the gloves formed by the method. In particular, the invention relates to a coated glove having a lubricous coating to assist in applying orthopaedic bandages of the type having an uncured resin coating thereon.

BACKGROUND OF THE INVENTION

Plaster of paris casts have been used to immobilize body members for some time. These bandages are made by depositing plaster of paris on a reinforcing scrim material such as gauze. When the plaster of paris is dipped in water, reactions take place which result in the hardening of the cast material. Plaster of paris casts, however, suffer from a number of disadvantages. X-ray transmission through the cast to determine whether a fracture has properly set is extremely difficult. In addition, the cast is quite heavy and restricts the mobility of patients wearing the cast.

In order to overcome the disadvantages of plaster of paris casts, numerous attempts have been made to develop plastic or plastic-reinforced material as replacements for plaster of paris. U.S. Pat. Nos. 3,241,501 and 3,881,473 disclose casts which are made with a flexible fabric impregnated with a polymer which is capable of being cured by ultraviolet light.

Other attempts to replace plaster of paris casts are disclosed in German Offenlegenscrift Nos. 2353212 and 2357931, U.K. Patent No. 1,578,895 and PCT Application No. WO81/00671. These bandages are open-weave fabrics coated with polyurethane prepolymers, that is, reaction products of isocyanates and polyols. The bandages are dipped into water in the same manner as the plaster of paris and then applied to the limb of the patient. The water causes the prepolymer to polymerize and form a rigid polymer structure.

More recently, it has been found that in working with such materials having prepolymer resin coating that the tackiness of the resin of the bandage can make working with the bandages difficult and cumbersome for the doctor. In an attempt to address this issue, a glove lubricant comprised of water, sorbitol, mineral oil and silicone fluid has been sold by 3-M Company, St. Paul, Minn., under the tradename Cast Cream ™ with instructions to apply the lubricant to the gloves of one applying an isocyanate-functional prepolymer coated cast after wrapping of the cast but before molding of the cast to avoid having the exposed casting material adhere to the gloves of the one applying the cast. This is disclosed in the background of U.S. Pat. Nos. 4,667,661 and 4,774,937.

The '661 and '937 patents are directed to addressing the adherence issue by providing the resin itself with a lubricant. The curable resin-coated sheet is prelubricated with a lubricant which is either a) bonded to the resin; b) added to resin or applied to the surface of the coated sheet; or c) provided in a combination of the bonding and surface application described. In many instances, however, the tacky feature of the orthopaedic bandage is desirable. As by way of example, when the applier is attempting to get the end of the bandage to stick to the surface of the bandage wrap in order to terminate the application of the bandage. The addition of lubricant in the resin permits relative slipping of the resin-coated sheet and requires molding the cast in position and holding it in position to prevent slippage.

Coatings for substrates having a lower coefficient of friction have been shown in U.S. Pat. No. 4,100,309 entitled, "Coated Substrate Having a Low Coefficient of Friction Hydrophilic Coating and a Method of Making the Same". That reference describes a substrate which is coated with a polyvinylpyrrolidone-polyurethane interpolymer. Copending commonly assigned U.S. patent application Ser. No. 726,449, filed Jul. 8, 1991, entitled, "Method of Applying an Orthopaedic Bandage" discloses the use of a polyvinylpyrrolidone coated glove in the application of resinous substrate casting materials. Although the invention described in that application represents a significant advance in the science of orthopaedic bandages, there have been certain shortcomings discovered regarding those gloves. The glove described in the patent application in many instances perform too well. That is, the slipperiness of the gloves is present to such a great extent that ancillary manipulation is restricted. The ability of the applier of the casting material to handle pens and other utensils or to tear open foil packages to access the casting material is greatly restricted by the extreme slipperiness of the gloves. Furthermore, the durability of the gloves is at a point that is less than optimum.

Polyvinyl alcohol coated gloves have been found to have acceptable durability and slip levels but many coated gloves heretofore known require uneconomical high temperature methods of manufacture. Furthermore, the preferred, or most effectual thermally, reversible gelling agent used in existing polyvinyl alcohol glove manufacture is toxic and not applicable to medical glove applications.

SUMMARY OF THE INVENTION

The invention herein described allows a coating to be applied at room temperatures and with a conventional dipping apparatus using dip parameters that dry and cure onto a rubber latex substrate in sequences and times readily adaptable to conventional dip equipment. The coatings established in this manner have adequate adhesion to the rubber substrate. The gloves can be readily removed from the molds and have the following in-use attributes:

a) the coated gloves do not adhere to tacky urethane prepolymer coated tapes;

b) the coating remains functional through the application of a desired number of tapes;

c) the coating when wetted with water has a preferred balance of slip-to-grip which allows smooth objects to be picked up, handled and, when desired, gripped, i.e., pens and instruments, and the coating permits the tearing open and manipulation of foil packages;

d) although the coating imbibes water when wet, it is less prone to self-adhesion than are existing polyvinylpyrrolidone constructions. This reduces the incidence of blocking in high humidity conditions and self-adhesion; and the wet polyvinyl alcohol overdip of the present invention is compounded to be very thixotropic by incorporating a rhamsan gum. Relatively high levels of the predissolved rhamsan gum allows the manufacture of the gloves without any of the runback or dripoff problems usually associated with uncoagulated dips in glove manufacture.

In order to be an acceptable coating for the uses intended herein, the glove and coating must a) not be too brittle when dry, this would manifest itself in a cracking and flaking of the coating on the area of the gloves that are elongated the most, i.e., the cuff end of the coating which is stretched during donning to pull the glove over the thumb; b) the coating must not be too slippery when wet and must maintain a sufficient amount of the cross-linking when wet to prevent the coating from dissolving off the glove when in use with the casting tape; c) the coating must have sufficient thickness or staying power to process a desired number of tapes of the casting tape material; d) the coating is preferably applied at approximately ambient temperatures or, at a minimum, temperatures below 70° C.; and e) the coating should have a sufficiently low cost.

Polyvinyl alcohol solutions in water tend to be newtonian and flow excessively at most viscosities. Incorporation of a predetermined amount of rhamsan gum as a thickener effectively deposits a layer of the compound that does not drip off or flow back after the shear imposed during the dipping has occurred. Stopping the runback or excessive drain-off tendencies of the polyvinyl alcohol solutions results in gloves that are aesthetically acceptable and do not contribute to manufacturing problems of the running, non-thickened material. This ability to control the rheology allows the selection of an optimum ratio of contributing ingredients and allows deposition on the rubber substrate from a cold or unheated dip tank.

Therefore, it has been found that the incorporation of a thickening agent in the polyvinyl alcohol solutions used during a dipping process to coat a glove creates a glove having adequate physical characteristics while easing the manufacturing process. In mixtures formulated to have practical mixing and transfer characteristics applicable to dipping less than 0.35% rhamsan gum of the total contained water may slow runbacks but does not immobilize them, and mixtures having from 0.35% to 0.60% rhamsan gum of the total contained water effectively stops post-dipping drips and runbacks. Runbacks tend to occur because the glove forms used in the manufacturing process are often rotated 180° up to invert the form to cause an evening of the coating. If the substance applied flows too readily, it will flow back over the form and remain on the form after stripping of the glove thus providing a glove having a messy overdrip present which interferes with the manufacturing process.

BRIEF DESCRIPTION OF THE DRAWINGS

The invention will be described with reference to the accompanying drawings wherein:

FIG. 1 is a block diagram of the process for making the gloves of the present invention.

DETAILED DESCRIPTION OF THE INVENTION

Figure 2A:
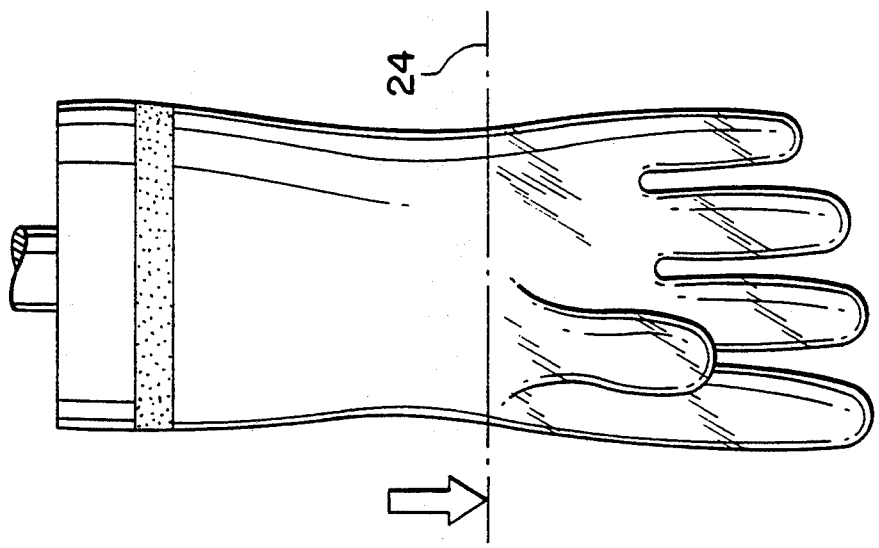
FIG. 2, a–c, is a schematic diagram showing the level of dip on the glove form of the various constituent parts of the process.

With reference to FIG. 1, there is shown a block diagram of a general glove-making process initially using the forms which may be forms as described in U.S. Pat. Nos. 4,047,251 and 4,135,867 to Stockum. The form is cleaned 10 prior to initiation of the manufacturing process in order to assure a good forming surface, and the form is passed through an oven 11 to preheat the form. The form itself is dipped into a coagulant tank 12 containing a latex coagulant usually a solution of calcium nitrate and alcohol or calcium nitrate and water. The form is removed from the coagulant tank and proceeds through a drying oven 13. The form, at this time, may be manipulated and rotated 180 degrees into an up-right position in order to cause an evening of the coagulant layer prior to drying. The form with the dry coagulant thereon is then immersed into a latex solution 14. The presence of the coagulant causes the latex compound to deposit on the form and the form is removed from the latex solution tank. After removal from the latex solution tanks, the form is often manipulated again into an upright position or otherwise in order to evenly distribute the latex compound about the form while the coagulant affects the latex in order to gel the latex film. This rotation equalizes any wet latex runs and assures a more uniform overall gauge in the finished glove. The film is caused to gel more completely by transferring the form through a gelling oven 15 which gels the layer.

After gelling of the latex film layer, the form and layer are immersed in a leaching tank 16 or tanks. This leaching tank 16 contains hot water which is used to remove any water-soluble materials from the deposit. The gloves are then dipped in the lubricous coating of the present invention in a polyvinyl alcohol solution overdip tank 17. The forms are then again transferred through a curing oven 18 to cure the polyvinyl alcohol coating thereon. Optionally, the forms may then be dipped into a powdered dip parting agent tank 19 containing a slurry of powder and liquid. The forms are then removed and again dried in an oven 20 in order to remove the liquid thus leaving the powder coating. The gloves are then manually removed from the forms 21, a process which entails grasping the cuff of the glove and stripping it downward over the fingertips. This process inverts the gloves which must, therefore, be inverted in order to expose the polyvinyl alcohol coated side of the gloves in the outward direction.

It is, therefore, easily seen that the process by which the gloves are made is essentially a series of tanks and associated ovens into which a ceramic or plastic form in the shape of a hand is serially dipped. Each tank contains one of a solution, slurry or latex. The amount of liquid picked up by the forms depends on the percent solids, viscosity and times of immersion and withdrawal from each tank. In the current invention, an overdip solution is utilized to give controlled slip to the final finished glove. The viscosity of this overdip is controlled by the use of a surprisingly large amount of rhamsan gum and is applied at room temperature.

Figure 2B:
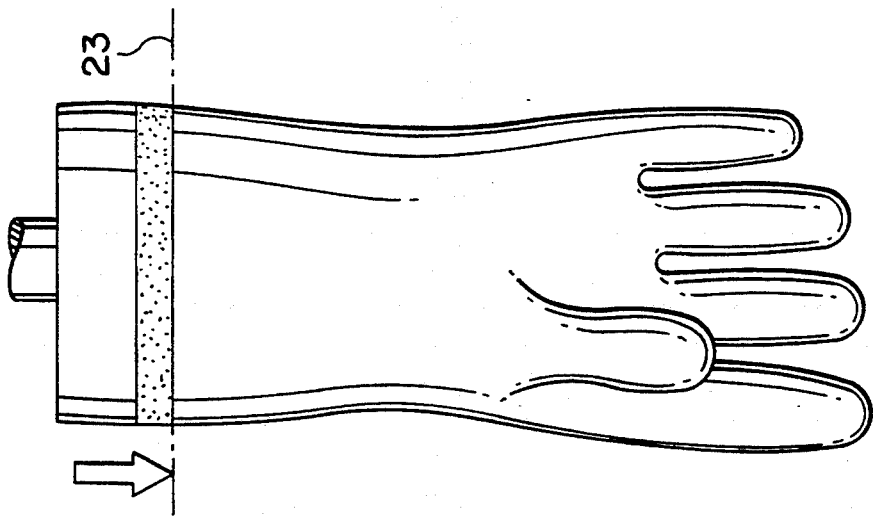
Figure 2C:
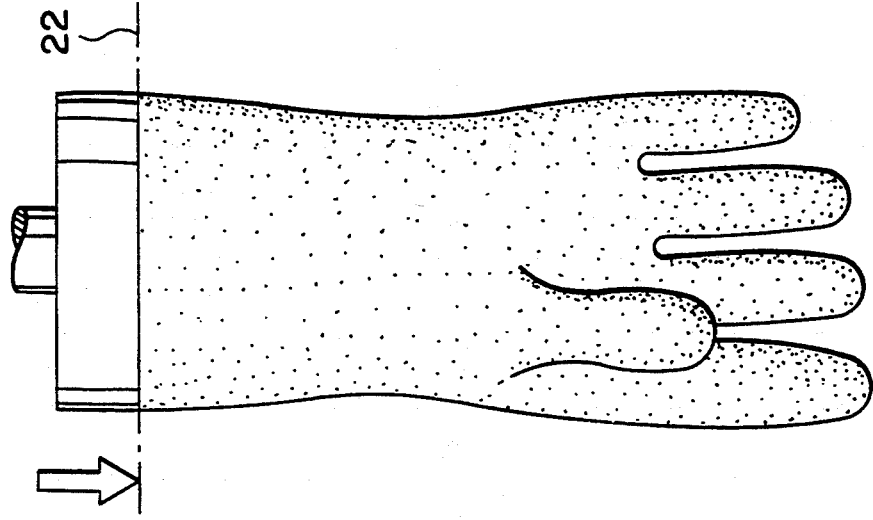

Referring now to FIGS. 2a, 2b and 2c, it is noted that during the process, the form is dipped into the coagulant tank to a level 22. This level is at a point higher on the glove form than the level 23 to which the form is dipped into the latex (FIG. 2b). Finally, in the polyvinyl alcohol lubricous coating overdip tank, the form is only dipped preferably to a level which covers the fingers and a first portion of the palm at a level 24 (FIG. 2c). By dipping the glove form into the coagulant at a level greater than the level intended to dip the form into the latex solution, it is assured that coagulant will be present in order to coagulate the latex onto the form at least to the level selected. The preferred embodiment having a polyvinyl alcohol overdip which only includes the fingers and a portion of the palm, creates a lubricous surface on the most active portions of the glove while leaving some portions uncoated to permit some degree of frictional control.

The following are examples of overdip formulations used to provide the lubricous coating. In the following examples, it should be noted that the rhamsan gum is shown often having weight which is the same in both the wet and dry form. This is due to the fact that the rhamsan gum is predissolved in water. This is consistent with latex formula understood by those of ordinary skill in the art. The reference to glutaraldehyde in the dry form is not necessarily dry in the strictest physical sense. The glutaraldehyde is referenced to be considered in the 100% active form. Formula presented in this manner should allow a technician to ascertain the ratio of dry ingredients in the dried film occurring on the glove as well as to determine the percent of residual solids left after drying and curing.

The PVA normally used in the examples is designated by the trade designation D2702 available from H. B. Fuller Company. This product code identifies a fully hydrolyzed grade of PVA and may be represented by Air Products, Airvol 325-350 series. The PVA may contain a small percentage of bacteriostat and a defoamer in the proprietary mixtures. The references to Cab-O-Sperse A-1695 refer to a colloidal dispersion of fumed silica in water. This dispersion is ph adjusted with ammonium hydroxide. This material is available from the Cabot Corp., Cab-O-Sil Division. Igepal CO-630 is a surfactant of the othoxylated nonyl alcohol type. Some of the formulations contained a commercial grade polyvinyl acetate available from H. B. Fuller under the designation HBF 3996.

Example 1

|  | % SOLIDS | DRY WT. | WET WT. | % DRY |
|---|---|---|---|---|
| Water |  | — | 55.95 | 0 |
| Rhamsan Gum K7C233 | (100%) | 0.45 | 0.45 | 3.8 |
| Glutaraldehyde | (50%) | 0.08 | 0.16 | 0.7 |
| Polyvinyl Alcohol D2702 | (10%) | 3.45 | 34.56 | 29.1 |
| A-1695 SiO$_2$ Cab-O-Sperse | (17%) | 0.20 | 1.20 | 1.7 |
| Igepal CO-630 | (100%) | 0.04 | 0.04 | 0.3 |
| Glycerin | (100%) | 7.64 | 7.64 | 64.4 |
| 11.87% total solids |  | 11.87 | 100.0 | 100.0 |

The above mixture provided good quality gloves without significant runback or overrun of the dipping solution. The gloves were lubricous when wet but provided the wearer with sufficient tactile friction in order to manipulate small items such as pens and instruments.

Example 2

|  | % SOLIDS | DRY WT. | WET WT. | % DRY |
|---|---|---|---|---|
| Rhamsan Gum K7C233 | (0.73%) | 4.85 | 664.0 | 1.3 |
| Polyvinyl Alcohol D2702 | (10%) | 216.0 | 2160.0 | 59.2 |
| HBF 3996 Polyvinyl Acetate | (55%) | 132.0 | 240.0 | 36.2 |
| A-1695 SiO$_2$ Cab-O-Sperse | (17%) | 11.7 | 69.0 | 3.2 |
| 11.6% solids |  | 364.6 | 3133.0 | 99.9 |

Example 2 provided poor results. The runoff of the overdip solution after the formed glove on the mold was rotated to a vertical position led to undesirable coating of the mold above the glove area. This coating was, therefore, determined to be unsatisfactory.

Example 3

|  | % SOLIDS | DRY WT. | WET WT. | % DRY |
|---|---|---|---|---|
| Rhamsan Gum K7C233 | (0.73%) | 28.0 | 3928.5 | 7.2 |
| Polyvinyl Alcohol D2702 | (10%) | 216.0 | 2160.0 | 55.7 |
| HBF 3996 Polyvinyl Acetate | (55%) | 132.0 | 240.0 | 34.0 |
| A-1695 SiO$_2$ Cab-O-Sperse | (17%) | 11.7 | 69.0 | 3.0 |
| 6.1% solids |  | 387.7 | 6397.5 | 99.9 |

Example 3 provided a glove having a lubricous outer coating which maintained the sufficient tactile friction to manipulate small items.

Example 4

A mixture of 30 parts of a polyurethane latex, 20 parts polyvinylpyrrolidone and 50 parts polyvinyl alcohol in dry ratios was mixed in a solution with water having rhamsan gum as 0.296% of the total water. This overdip solution produced an acceptable film, but the runbacks on inversion of the glove were excessive.

Example 5

A mixture of 15 parts of a polyurethane latex, 10 parts polyvinylpyrrolidone and 75 parts polyvinyl alcohol in dry ratios was placed in a solution with water having rhamsan gum as 0.21% of the total water. This example produced acceptable film but, again, the runbacks were excessive.

Example 6

A mixture of 45 parts of a polyurethane latex, 30 parts polyvinylpyrrolidone and 25 parts polyvinyl alcohol in dry ratios was placed in a solution with water having rhamsan gum as 0.29% of the total water. This overdip produced an acceptable film, but, again, the runbacks were excessive.

Example 7

A mixture of 30 parts of a polyurethane latex, 20 parts polyvinylpyrrolidone and 50 parts polyvinyl alcohol in dry ratios was placed in a solution with water having rhamsan gum as 0.468% of the total water. This overdip produced an acceptable film and no runbacks on inversion of the mold.

Example 8

3.46 parts polyvinyl alcohol, 0.2 parts fumed silica and 3.82 parts glycerine in dry ratios was placed in a solution in total water having rhamsan gum present in 0.51% of the total water. This overdip produced an acceptable film with no runbacks.

Example 9

3.46 parts polyvinyl alcohol, 0.2 parts fumed silica and 7.65 parts glycerine in dry ratios was placed in a solution in water having rhamsan gum 0.49% of the total water. This overdip produced an acceptable film with no runbacks.

It has, therefore, been determined that in mixtures formulated to have practical mixing and transfer characteristics applicable to dipping, less than 0.35% rhamsan gum on the total contained water, may slow the runbacks but does not immobilize them. 0.35% to 0.60% rhamsan gum on the total contained water effectively stops post-dipping drips and runbacks, i.e., when the glove is rotated 180 degrees to the upright position.

The glycerine was present to provide a plasticizing function to the overdip once dried. This prevented or substantially reduced the amount of cracking and flaking of the coating caused by donning of the glove. The rhamsan gum thickened the solution sufficiently in order to prevent the drips and runbacks present in the unthickened solutions.

Thus, the invention has been described in detail with the appended claims directed to the invention. It should be clear to one of ordinary skill in the art that other modifications and other compounds may be added to the solutions without departing from the spirit and scope of the present invention.

What is claimed is:

1. A lubricous glove for use in applying substrates comprising:
    a) a base of elastomeric material defining an internal volume for receiving a hand of a wearer, said base having an outer surface; and
    b) said outer surface having a lubricous coating thereon comprising polyvinyl alcohol and thickener wherein the base of elastomeric material defines a finger portion, a palm portion and a wrist portion for receiving the fingers of a hand, the palm of a hand and the wrist of a hand, respectively, and the lubricous coating extends about the surface of the finger portion and a part of the palm portion and does not include the wrist portion of the elastomeric material.

2. A lubricous glove for use in applying substrates comprising:
    a) a base of elastomeric material defining an internal volume for receiving a hand of a wearer, said base having an outer surface; and
    b) said outer surface having a lubricous coating thereon comprising from about 20% to about 38% by weight polyvinyl alcohol and from 3% to 8% by weight rhamsan gum and from approximately 2% to approximately 5% by weight fumed silica and up to approximately 3% by weight glutaraldehyde.

3. A lubricous glove for use in applying substrates comprising:
    a) a base of elastomeric material defining an internal volume for receiving a hand of a wearer, said base having an outer surface; and
    b) said outer surface having a lubricous coating thereon comprising from about 20% to 38% by weight polyvinyl alcohol, from 3% to 8% by weight rhamsan gum, from approximately 2% to approximately 5% by weight fumed silica and from about 10% to about 50% polyvinyl acetate.

* * * * *